(12) United States Patent
Brown

(10) Patent No.: US 7,893,071 B2
(45) Date of Patent: Feb. 22, 2011

(54) SYNTHESIS AND EVALUATION OF NOVEL PHTHALIMIDE MIMICS AS ANTI-ANGIOGENIC

(75) Inventor: Milton L. Brown, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 411 days.

(21) Appl. No.: 10/475,363

(22) PCT Filed: Apr. 22, 2002

(86) PCT No.: PCT/US02/12655

§ 371 (c)(1),
(2), (4) Date: Oct. 21, 2003

(87) PCT Pub. No.: WO02/086078

PCT Pub. Date: Oct. 31, 2002

(65) Prior Publication Data
US 2004/0122030 A1    Jun. 24, 2004

Related U.S. Application Data

(60) Provisional application No. 60/285,745, filed on Apr. 23, 2001, provisional application No. 60/338,955, filed on Dec. 10, 2001.

(51) Int. Cl.
A01N 43/54 (2006.01)
A61K 31/517 (2006.01)
C07D 239/88 (2006.01)
C07D 401/04 (2006.01)

(52) U.S. Cl. ............ 514/266.2; 514/266.3; 514/266.31; 544/284; 544/285; 544/287

(58) Field of Classification Search .............. 514/266.3, 514/312, 415, 417, 266.31, 266.2; 544/287, 544/284, 285; 546/137; 548/361.5
See application file for complete search history.

(56) References Cited

U.S. PATENT DOCUMENTS

| | | | | |
|---|---|---|---|---|
| 3,567,827 A | * | 3/1971 | Stearus | 514/266.31 |
| 4,159,330 A | * | 6/1979 | Doria et al. | 514/266.2 |
| 4,183,931 A | * | 1/1980 | Wolfe et al. | 514/266.21 |
| 4,379,788 A | * | 4/1983 | Heider et al. | 514/264.1 |
| 4,390,697 A | * | 6/1983 | Tully | 544/251 |
| 4,431,440 A | * | 2/1984 | Bhalla et al. | 504/240 |
| 4,480,096 A | * | 10/1984 | Fletcher | 544/289 |
| 4,668,682 A | * | 5/1987 | Sekiya et al. | 514/266.2 |
| 5,055,580 A | * | 10/1991 | Dietz et al. | 544/233 |
| 5,147,875 A | * | 9/1992 | Coates et al. | 514/266.31 |
| 5,482,941 A | * | 1/1996 | Terrett | 514/252.17 |
| 5,593,990 A | | 1/1997 | D'Amato | |
| 5,929,081 A | | 7/1999 | Brown et al. | |
| 6,028,075 A | | 2/2000 | Pines et al. | |
| 6,235,756 B1 | | 5/2001 | D'Amato | |
| 6,355,636 B1 | | 3/2002 | Wissner et al. | |
| 6,429,212 B1 | | 8/2002 | Hashimoto | |
| 6,429,221 B1 | | 8/2002 | Muller | |
| 6,515,129 B1 | | 2/2003 | Hashimoto | |
| 6,844,359 B2 | | 1/2005 | Muller | |
| 2003/0187024 A1 | | 10/2003 | D'Amato | |

FOREIGN PATENT DOCUMENTS

| | | |
|---|---|---|
| DE | 3220898 | * 12/1983 |
| EP | 0686625 A1 | 12/1995 |
| EP | 0887340 A1 | 12/1998 |
| EP | 0 930 067 A2 | 7/1999 |
| EP | 0930067 A2 | 7/1999 |
| JP | 08-188563 | 7/1996 |
| JP | 10-072346 | 3/1998 |
| JP | 10-081666 | 3/1998 |
| JP | 10072346 A2 | 3/1998 |
| JP | 10081666 A2 | 3/1998 |
| JP | 10-109975 | 4/1998 |
| JP | 10109975 A2 | 4/1998 |
| JP | 10-231285 | 9/1998 |
| JP | 10231285 A2 | 9/1998 |
| JP | 10-511946 | 11/1998 |
| JP | 11-035559 | 2/1999 |

(Continued)

OTHER PUBLICATIONS

Jiang J.B. et. al., J. Med. Chem., (1990), vol. 33, No. 6, pp. 1721-1728.*

(Continued)

*Primary Examiner*—James O Wilson
*Assistant Examiner*—Tamthom N Truong
(74) *Attorney, Agent, or Firm*—Schwegman, Lundberg & Woessner, P.A.

(57) ABSTRACT

The present invention is directed to novel thalidomide derivative compounds that have activity as anti-angiogenic compounds. More particularly the compounds have the general structure: where $R_1$ is selected from the group consisting of H, halo, alkyl, haloalkyl, $-NH_2$, hydroxy and alkoxy; $R_2$ is selected from the group consisting of optionally substituted bicyclic, optionally substituted aryl, and $R_6$ is H, or $C_1$-$C_8$ alkyl; $R_{19}$ is optionally substituted aryl; and m is 0-6.

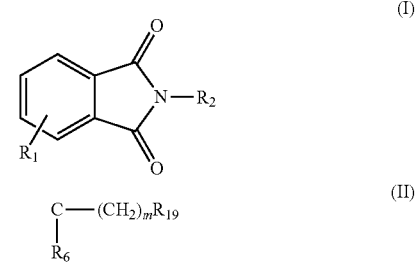

4 Claims, No Drawings

FOREIGN PATENT DOCUMENTS

| | | |
|---|---|---|
| WO | WO-9620926 A1 | 7/1996 |
| WO | WO-9729079 A1 | 8/1997 |
| WO | WO 98/07421 | 2/1998 |
| WO | WO-9807421 A1 | 2/1998 |
| WO | WO-9852919 A1 | 11/1998 |
| WO | WO-9900121 A1 | 1/1999 |
| WO | WO 01/34606 A1 | 5/2001 |
| WO | WO-0134606 A1 | 5/2001 |

OTHER PUBLICATIONS

Kenyon, B. M., Browne, F. and D'Amato, R. J. (1997). "Effects of Thalidomide and Related Metabolites in a Mouse Corneal Model of Neovascularization". Exp. Eye Res. vol. 64, pp. 971-978.

D'Amato, R. J., Loughnan, M. S., Flynn, E. and Folkman, J. (1994). "Thalidomide is an inhibitor of angiogenesis". Proc. Natl. Acad. Sci. USA. vol. 91, pp. 4082-4085.

Ching, L-M et al., (1998). "Interaction of thalidomide, phthalimide analogues of thalidomide and pentoxifylline with the anti-tumour agent 5,6-dimethylxanthenone-4-acetic acid: concomitant reduction of serum tumour necrosis factor-alphan and enhancement of antitumour activity", British J. of Cancer, 78(3), pp. 336-343.

Shimazawa, R., et al, (1999). "Antiangiogenic Activity of Tumor Necrosis Factor-alpha Production Regulators Derived from Thalidomide", Biol. Pham. Bull., 22(2), pp. 224-226.

Hamel, E. et al., (1996). "Antitumor 2,3 Dihydro-2-(aryl)-4(1H)-quinazolinone Derivatives," Biochemical Pharmacology, vol. 51, pp. 53-59.

Ching, L M., "Interaction of Thalidomide, Phtalimide Analogues of Thalidomide Pentoxifylline with the Antitumor Agent 5,6-Dimethylxanthenone-4-Acetic Acid", *British Journal of Cancer*, 78(3), (Aug. 1998),336-343.

Hamel, E. , et al., "Antitumor 2, 3- Dihydro-2-(aryl)-4(1H)-quinazolinone Derivatives", *Biochemical Pharmacology*, vol. 51(1), (1996),53-59.

Meegalla, S. K., et al., "Synthesis and Pharmacological Evaluation of Isoindolo (1,2-b)quinazolinone and Isoindolo(2,1-a)benzimidazole Derivatives Related to the Antitumor Agent Batracylin", *Journal of Medicinal Chemistry*, 37(20), (1994),3434-3439.

Sasaki, K. , et al., "Benzylphthalimides and phenethylphthalimides with thalidomide-like activity on the production of tumor necrosis factor alpha.", *Biol Pharm Bull.*, 18(9), (1995),1228-33.

Shimazawa, R. , "Antiangiogenic Activity of Tumor Necrosis Production Regulators Derived from Thalidomide", *Biological & Pharmacological Bulletin*, 122(2), (Feb. 1999),224-226.

Teodori, E. , et al., "Design,Synthesis, and in Vitro Activity of Catamphiphilic Reverters of Multidrug Resistance: discovery of a Selective, highly Efficacious chemosensitizer with Potency in the Nanomolar Range,", *Journal of Medicinal Chemistry*, 42(10), (1999),1687-1697.

Vamecq, J. , et al., "Synthesis and Anticonvulsant and Neurotioxic Properties of Substituted N-Phenyl Derivatives of the Phthalimide Pharmacophore", *Journal of Medicinal Chemistry*, 43(7), (2000),1311-1319.

"Canadian Application No. 2,444,704, Office action mailed Jul. 17, 2009", 2 pgs.

"Canadian Application No. 2,444,704, Response filed Jan. 18, 2010 to Office action mailed Jul. 17, 2009", 9 pgs.

"European Application No. 02726787.1, Office Action Mailed Dec. 3, 2009", 5 pgs.

* cited by examiner

SYNTHESIS AND EVALUATION OF NOVEL PHTHALIMIDE MIMICS AS ANTI-ANGIOGENIC

RELATED APPLICATIONS

This application is a national stage filing of International Application No. PCT/US02/12655, filed Apr. 22, 2002, which claims priority under 35 USC §119(e) to U.S. Provisional Application Ser. No. 60/285,745, filed Apr. 23, 2001 and 60/338,955, filed Dec. 10, 2001, the disclosures of which are incorporated herein.

FIELD OF THE INVENTION

The present invention is directed to novel substituted phthalimide and isoquinoline derivatives, and the use of such derivatives as therapeutic agents. These compounds have been discovered to have anti-angiogenic activity.

BACKGROUND OF THE INVENTION

Inappropriate angiogenesis is the cause or an aggravating factor in numerous disease states. For example, age related macular degeneration (ARMD) refers to a condition that steals away central vision but leaves peripheral (side) vision intact. This disease can be present in several forms and affects approximately 1 out of 5 individuals over the age of 65 and 1 out of 4 over the age of 75. That represents approximately 20 million Americans.

There are two forms of macular degeneration: dry macular degeneration and wet macular degeneration. The dry form, in which the cells of the macula slowly begin to break down, is diagnosed in 90 percent of macular degeneration cases. It may occur in one eye or both. The wet form, although it only accounts for 10 percent of the cases, results in 90 percent of the blindness. As the wet form worsens, patients begin to have abnormal blood vessels growing behind the macula. These vessels are very fragile and will leak fluid and blood (hence 'wet' macular degeneration), causing rapid damage to the macula. As of yet no specific pharmacological treatments are available.

The wet form of ARMD and other ocular diseases caused by the formation of new blood vessels (neovascularization) are among the leading causes of blindness. Thus there is a great need for the discovery of new drugs to treat such ocular diseases. One approach is to administer pharmaceutical anti-angiogenic agents to prevent the inappropriate neovascularization.

Novel anti-angiogenic compounds also have utility as anti-cancer agents. Malignancies are characterized by the growth and spread of tumors. One important factor in the progression of this disease is angiogenesis, a complex process in which capillary blood vessels grow in an ordered sequence of events. Once a tumor has started, every increase in tumor cell population must be preceded by an increase in new capillaries that converge on the tumor and supply the cells with oxygen and nutrients. Tumors may thus remain harmless and confined to their tissue of origin, as long as an accompanying angiogenic program is prevented from being activated. Since the angiogenesis-dependent step in tumor progression is shared by solid tumors of all etiologies, the ability to inhibit tumor-associated angiogenesis is a promising approach in combating cancer.

A substantial body of experimental evidence supports the hypothesis that tumor angiogenesis is fundamental for the growth and metastasis of solid tumors [Folkman, J. Natl. Cancer Inst., Vol. 82, pp. 4-6 (1989); N. Weidner, et al., Amer. J. Pathol., Vol. 143, pp. 401-409 (1993)]. Indeed, the majority of solid tumors are not even clinically detectable until after the occurrence of neovascularization, whose induction in solid tumors is mediated by one or more angiogenic factors.

Furthermore, angiogenesis is also important in a number of other pathological processes, including arthritis, psoriasis, diabetic retinopathy, chronic inflammation, scleroderma, hemangioma, retrolental fibroplasia and abnormal capillary proliferation in hemophiliac joints, prolonged menstruation and bleeding, and other disorders of the female reproductive system.

Accordingly, there is a need for compounds that have activity as anti-angiogenic agents and can be safely administered to patients to treat angiogenic-associated diseases. The present invention relates to a composition, comprising an anti-angiogenic compound, for use in treating angiogenic-associated diseases, as well as malignancies, including inhibition of primary tumor growth, tumor progression and metastasis. More particularly, the present invention is directed to thalidomide derivatives and their use as anti-angiogenic compositions.

Thalidomide was originally prescribed as a sedative, however its use was discontinued when it was found to be a potent teratogen, causing serious birth defects, especially affecting limb development. The dysmelia (limb defects) seen with thalidomide is proposed to be caused by an inhibition of blood vessel growth in the developing fetal limb bud. Although this affect is vasculogenic (affecting the formation of a capillary bed), studies have demonstrated that thalidomide is also anti-angiogenic (affecting the formation of new blood vessels from sprouts of pre-existing vessels). Thalidomide is relatively nontoxic, when taken by nonpregnant adults and is now in phase 2 clinical trials as a potential anti-cancer agent as well as a treatment for vascular eye diseases such as diabetic retinopathy, retinopathy of prematurity, and macular degeneration.

Thalidomide has been reported by Folkman, et. al. (PNAS, 91(9):4082-5, 1994) as having significant anti-angiogenic efficacy. The effects of thalidomide on corneal angiogenesis induced by vascular endothelial growth factor (VEGF), has been reported (Kruse et al, Graefes Archive for Clinical & Experimental Ophthalmology. 236(6):461-6, 1998). In Kruse et al, corneal neovascularization was induced in rabbits by an intrastromal pellet loaded with 500 or 750 ng VEGF. Animals receiving two daily feedings of 200 mg/kg of thalidomide, responded with statistically significant inhibition (P<0.0001) of corneal angiogenesis after the 5th day of treatment. This observation indicates that thalidomide has a significant anti-angiogenic effect against VEGF-induced ocular neovascular growth.

Thalidomide has also demonstrated inhibitory effects on angiogenesis in the basic fibroblast growth factor (bFGF) induced rabbit corneal micropocket assay and orally in mice models (Joussen et al. Graefes Archive for Clinical & Experimental Ophthalmology, 237(12):952-61, 1999 and Kenyon et al., Experimental Eye Research. 64(6):971-8, 1997). Thalidomide and a thalidomide analog (cc-1069) have been reported to inhibit the in vitro proliferation of endothelial cells (cells which make up the vascular system). The results of this study revealed a significant decrease in endothelial cell proliferation in cultures treated with thalidomide and/or cc-1069. Taken together, these data support a strong correlation between the anti-angiogenic potential and inhibition of endothelial cell proliferation for thalidomide.

Studies reveal that the S(−)-enantiomer of thalidomide has the strongest anti-angiogenic activity in both VEGF-induced and bFGF-induced corneal neovascularization. This enantioselective preference lends support to a possible receptor mediated mechanism. The present invention is directed to a novel series of thalidomide analogs and the use of such analogs as inhibitors of angiogenesis. More particularly, the thalidomide analogs of the present invention lack the piperidine-2,6-dione moiety of thalidomide.

SUMMARY OF THE INVENTION

The present invention is directed to compounds having a general structure:

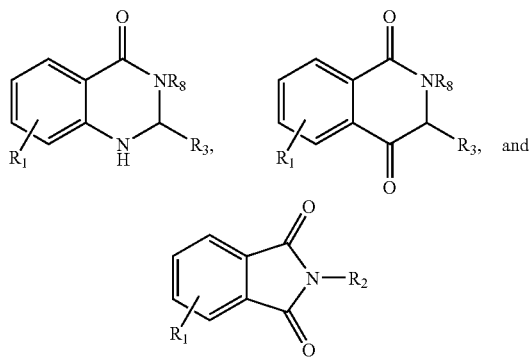

wherein $R_1$ is selected from the group consisting of H, halo, alkyl, haloalkyl, $-NR_5R_6$, hydroxy and alkoxy;

$R_2$ is selected from the group consisting of optionally substituted bicyclic, optionally substituted aryl, and

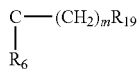

$R_3$ is selected from the group consisting of alkyl, phenyl, substituted phenyl, benzyl and substituted benzyl;

$R_8$ is selected from the group consisting of H or $C_1$-$C_6$ alkyl, or $R_8$ and $R_3$ taken together, can form, with the adjacent ring, an optionally substituted 5- or 6-membered aryl;

$R_5$ and $R_6$ are independently H, or $C_1$-$C_8$ alkyl;

$R_{19}$ is optionally substituted aryl; and m is 0-6. The present invention also encompasses compositions comprising those compounds and the use of such compositions for inhibiting angiogenesis.

DETAILED DESCRIPTION OF THE INVENTION

Definitions

In describing and claiming the invention, the following terminology will be used in accordance with the definitions set forth below.

As used herein, the term "purified" and like terms relate to the isolation of a molecule or compound in a form that is substantially free of contaminants normally associated with the molecule or compound in a native or natural environment.

As used herein, the term "treating" includes prophylaxis of the specific disorder or condition, or alleviation of the symptoms associated with a specific disorder or condition and/or preventing or eliminating said symptoms.

As used herein, the term "halogen" or "halo" means Cl, Br, F, and I. Especially preferred halogens include Cl, Br, and F. The term "haloalkyl" as used herein refers to a $C_1$-$C_4$ alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n is an integer refers to cyclic non-aryl group, for example $C_3$-$C_8$ cycloalkyl, represents cyclopropyl, cyclobutyl, cyclopentyl, cyclohexyl, cycloheptyl, and cyclooctyl.

The term "lower alkyl" as used herein refers to branched or straight chain alkyl groups comprising one to eight carbon atoms, including methyl, ethyl, propyl, isopropyl, n-butyl, t-butyl, neopentyl and the like.

As used herein, the term "optionally substituted" refers to from zero to four substituents, wherein the substituents are each independently selected. Each of the independently selected substituents may be the same or different than other substituents.

As used herein the term "aryl" refers to a mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one to three substituents, wherein the substituents, including alkyl, halo or amino substituents. The term ($C_1$-$C_8$ alkyl)aryl refers to any aryl group which is attached to the parent moiety via the alkyl group.

The term "heterocyclic group" refers to a mono- or bicyclic carbocyclic ring system containing from one to three heteroatoms wherein the heteroatoms are selected from the group consisting of oxygen, sulfur, and nitrogen.

As used herein the term "heteroaryl" refers to a mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, "effective amount" means an amount sufficient to produce a selected effect. For example, an effective amount of the phthalimide derivative is an amount of the compound sufficient to decrease endothelial cell proliferation, or decrease the growth rate of blood vessels, either in vivo or in vitro.

The term, "parenteral" means not through the alimentary canal but by some other route such as subcutaneous, intramuscular, intraspinal, or intravenous.

THE INVENTION

The present invention relates a novel series of substituted phthalimide and isoquinoline derivatives that are anticipated to have anti-angiogenic activity. More particularly, the invention is directed to a series of thalidomide derivatives wherein the piperidine-2,6-dione moiety has been replaced with other structures as shown below:

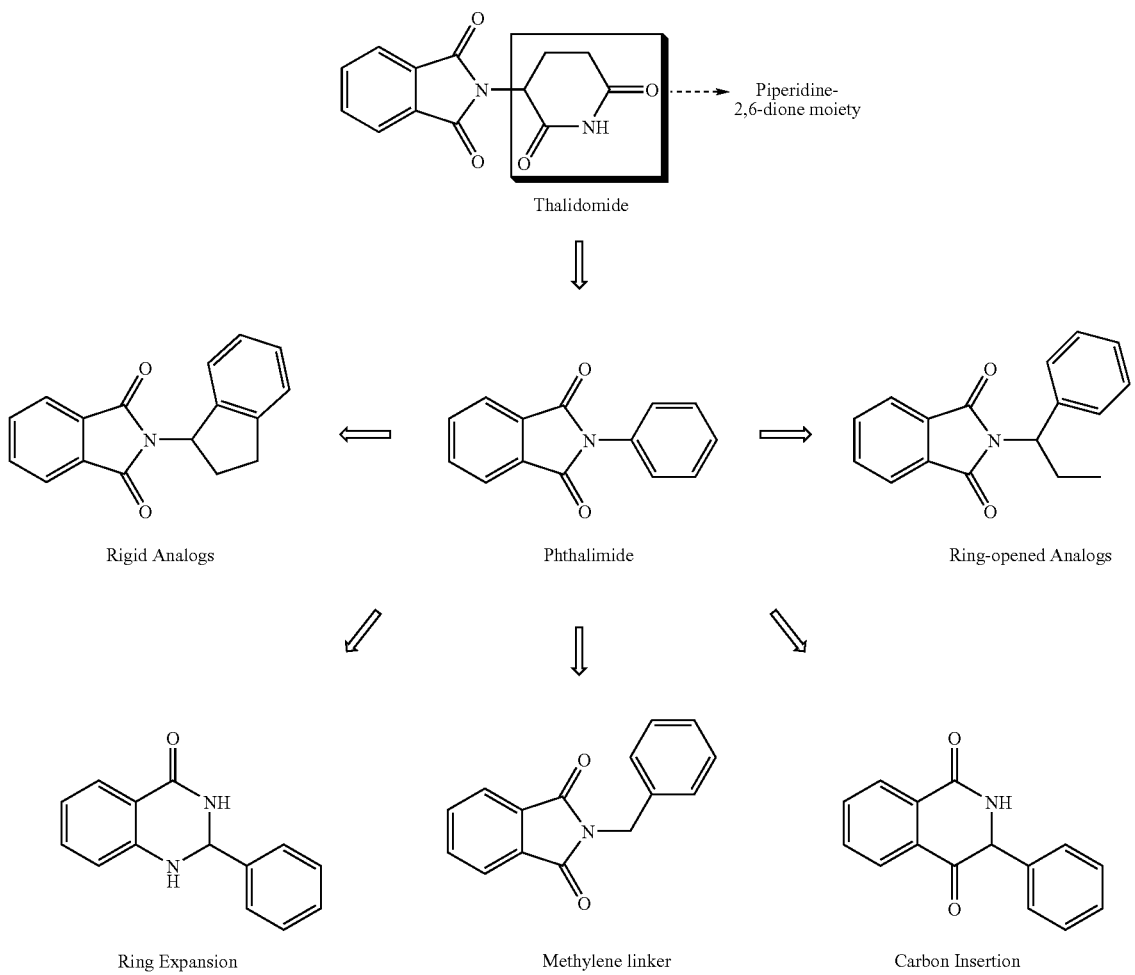

As used herein, the term "angiogenesis" means the generation of new blood vessels into a tissue or organ.

As used herein, the term "angiogenic-associated" disease or condition refers to a disease state or condition that is caused by, or aggravated by, inappropriate or excessive ageogenesis. For example, diseases that are considered angiogenic-associated include cancer as well as vascular eye diseases such as diabetic retinopathy, retinopathy of prematurity, and macular degeneration Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

In accordance with one embodiment a novel compound is provided having a general structure selected from the group consisting of:

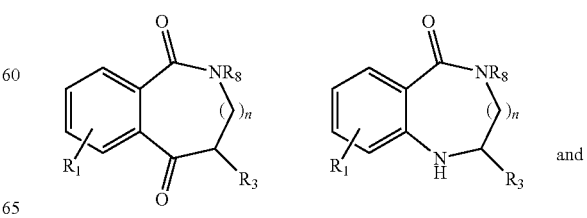

and

-continued

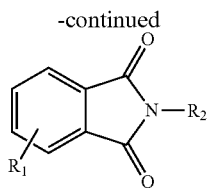

wherein $R_1$ is selected from the group consisting of H, halo, $C_1$-$C_8$ alkyl, $C_1$-$C_8$ haloalkyl, —$NR_5R_7$, hydroxy and $C_1$-$C_8$ alkoxy;

$R_2$ is selected from the group consisting of optionally substituted bicyclic, optionally substituted aryl, and

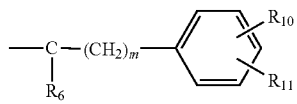

$R_3$ is selected from the group consisting of

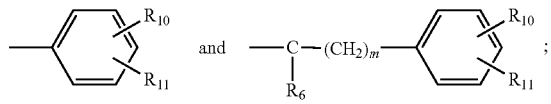

$R_8$ is selected from the group consisting of H, $C_1$-$C_8$ alkyl, or $R_3$ and $R_8$ taken together, can form, with the adjacent ring, an optionally substituted 5- or 6-membered aromatic ring;

$R_{10}$ and $R_{11}$ are independently selected from the group consisting of H, halo, $C_1$-$C_8$ alkyl, $C_1$-$C_8$ haloalkyl, —$NR_5R_7$, hydroxy and $C_1$-$C_8$ alkoxy or $R_{10}$ and $R_{11}$ taken together, can form, with the adjacent ring, an optionally substituted 5- or 6-membered aromatic ring;

$R_5$ and $R_7$ are independently H, or $C_1$-$C_8$ alkyl;

$R_6$ is selected from the group consisting of H, or $C_1$-$C_{12}$ alkyl, $C_2$-$C_8$ alkenyl and $C_2$-$C_8$ alkynyl;

n is an integer ranging from 0-2; and m is an integer ranging from 0-6.

In accordance with one embodiment the anti-angiogenic compound has the general structure:

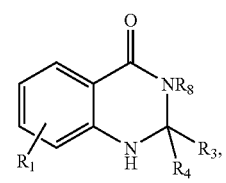 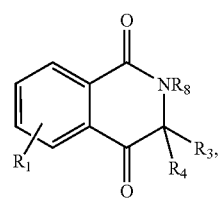

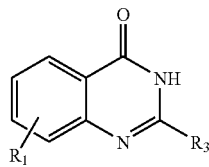 and 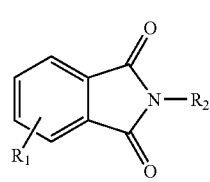

wherein $R_1$ is selected from the group consisting of H, halo, $C_1$-$C_4$ alkyl, carboxy and $C_1$-$C_8$ alkoxy;

$R_2$ is selected from the group consisting of

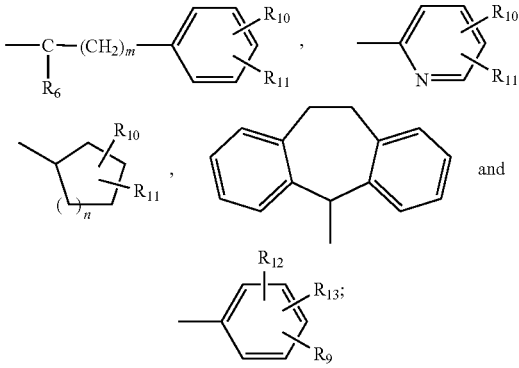

$R_3$ is selected from the group consisting of

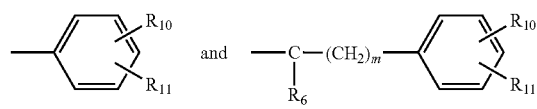

$R_8$ is selected from the group consisting of H, $C_1$-$C_8$ alkyl, or $R_3$ and $R_8$ taken together, can form, with the adjacent ring, an optionally substituted 5- or 6-membered heteroaryl;

$R_4$ is selected from the group consisting of H, $C_1$-$C_8$ alkyl, phenyl and benzyl;

$R_{13}$ and $R_9$ are independently selected from the group consisting of H, halo and $C_1$-$C_8$ alkoxy or $R_{13}$ and $R_9$ taken together, can form with the adjacent ring, an optionally substituted $C_5$-$C_6$ cycloalkyl or optionally substituted $C_5$-$C_6$ aromatic ring;

$R_{10}$ and $R_{11}$ are independently selected from the group consisting of H, halo, $C_1$-$C_8$ alkyl, $C_1$-$C_8$ haloalkyl, —$NR_5R_7$, hydroxy and $C_1$-$C_8$ alkoxy or $R_{10}$ and $R_{11}$ taken together, can form with the adjacent ring, an optionally substituted $C_1$-$C_6$ cycloalkyl or an optionally substituted $C_5$-$C_6$ aromatic ring;

$R_5$ and $R_7$ are independently H, or $C_1$-$C_8$ alkyl;

$R_6$ is selected from the group consisting of H, or $C_1$-$C_{12}$ alkyl, $C_2$-$C_8$ alkenyl and $C_2$-$C_8$ alkynyl;

$R_{12}$ is selected from the group consisting of H, halo, $C_1$-$C_4$ haloalkyl, —$NR_5R_6$, $C_1$-$C_8$ alkyl, hydroxy and $C_1$-$C_8$ alkoxy;

n is and integer from 1-3 and m is an integer ranging from 0-6. In one embodiment, $R_1$, $R_4$ and $R_8$ are each H, n is 1 and m is 0.

In accordance with one embodiment the anti-angiogenic compound has the general structure:

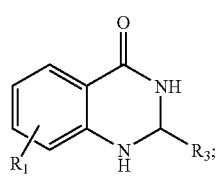 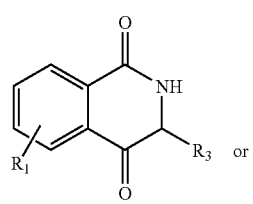 or

-continued

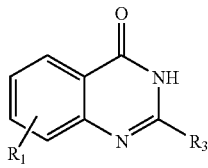

wherein $R_1$ is selected from the group consisting of H, halo, $C_1$-$C_8$ alkyl, hydroxy and $C_1$-$C_8$ alkoxy and $R_3$ is selected from the group consisting of

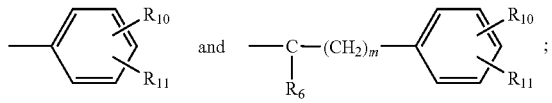

wherein $R_6$ is H, or $C_1$-$C_8$ alkyl; $R_{10}$ and $R_{11}$ are independently selected from the group consisting of H, halo, $C_1$-$C_8$ alkyl, $C_1$-$C_8$ haloalkyl, —$NR_5R_7$, hydroxy and $C_1$-$C_8$ alkoxy, or $R_{10}$ and $R_{11}$ taken together, can form with the adjacent ring, an optionally substituted $C_5$-$C_6$ cycloalkyl or $C_5$-$C_6$ aromatic ring; $R_5$ and $R_7$ are independently H, or $C_1$-$C_8$ alkyl; and m is an integer ranging from 0-6. In one embodiment, $R_1$ is H and $R_3$ is selected from the group consisting of phenyl;

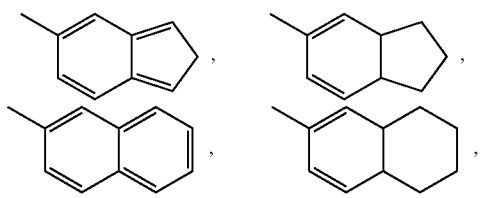

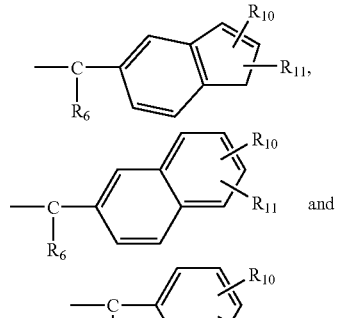

wherein $R_6$ is H, or $C_1$-$C_8$ alkyl; $R_{10}$ and $R_{11}$ are independently selected from the group consisting of H, halo, $C_1$-$C_8$ alkyl, $C_1$-$C_8$ haloalkyl, —$NR_5R_7$, hydroxy and $C_1$-$C_8$ alkoxy and $R_5$ and $R_7$ are independently H, or $C_1$-$C_8$ alkyl.

In accordance with one embodiment the anti-angiogenic compound has the general structure:

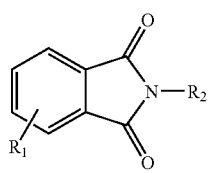

wherein $R_1$ is selected from the group consisting of H, halo, $C_1$-$C_8$ alkyl, hydroxy and $C_1$-$C_8$ alkoxy; and $R_2$ is selected from the group consisting of

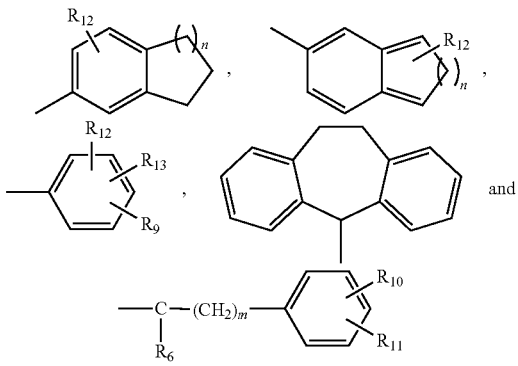

wherein $R_{10}$ and $R_{11}$ are independently selected from the group consisting of H, halo, $C_1$-$C_8$ alkyl, $C_1$-$C_8$ haloalkyl, —$NR_5R_7$, hydroxy and $C_1$-$C_8$ alkoxy or $R_{10}$ and $R_{11}$ taken together, can form with the adjacent ring, an optionally substituted $C_5$-$C_6$ cycloalkyl or optionally substituted $C_5$-$C_6$ aromatic ring;

m is an integer ranging from 0-3;

$R_5$ and $R_7$ are independently H, or $C_1$-$C_8$ alkyl;

$R_6$ is selected from the group consisting of H, $C_1$-$C_{12}$ alkyl, $C_2$-$C_8$ alkenyl and $C_2$-$C_8$ alkynyl;

$R_{12}$ is selected from the group consisting of H, halo, $C_1$-$C_4$ haloalkyl, —$NR_5R_6$, $C_1$-$C_8$ alkyl, hydroxy and $C_1$-$C_8$ alkoxy; and n is an integer ranging from 1-3.

In one embodiment the compound of the present invention has the general structure:

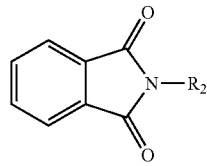

wherein $R_2$ is selected from the group consisting of

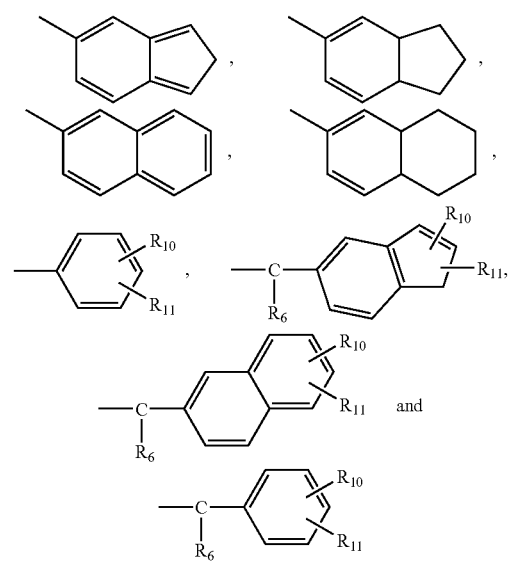

wherein $R_{10}$ and $R_{11}$ are independently selected from the group consisting of H, halo, $C_1$-$C_4$ haloalkyl, —$NR_5R_7$, hydroxy and $C_1$-$C_8$ alkoxy; and $R_5$ and $R_7$ are independently H, or $C_1$-$C_4$ alkyl;

$R_{12}$ is selected from the group consisting of H, halo and $C_1$-$C_8$ alkoxy; and $R_6$ is $C_1$-$C_8$ alkyl. In one preferred embodiment $R_2$ is selected from the group consisting of

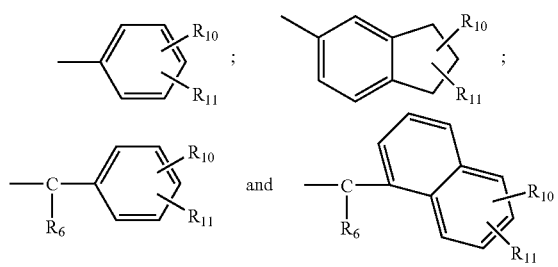

wherein $R_{10}$ and $R_{11}$ are independently selected from the group consisting of H, halo, and $C_1$-$C_8$ alkoxy.

In one preferred embodiment the compound has the structure:

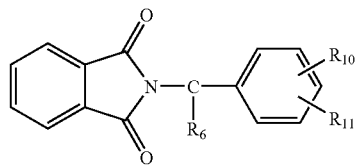

wherein $R_6$ is $C_1$-$C_8$ alkyl and $R_{10}$ and $R_{11}$ are independently selected from the group consisting of H and $C_1$-$C_4$ alkoxy, or $R_{10}$ and $R_{11}$ taken together, can form, with the adjacent ring, an optionally substituted 5- or 6-membered aromatic ring.

One aspect of the present invention is directed to a method of treating a angiogenic-associated disease or condition. More particularly, one embodiment of the present invention is directed to inhibiting undesired angiogenesis in a warm-blooded vertebrate, including humans. The method comprises the step of administering to the human or animal a composition comprising an effective amount of a compound of the general structure:

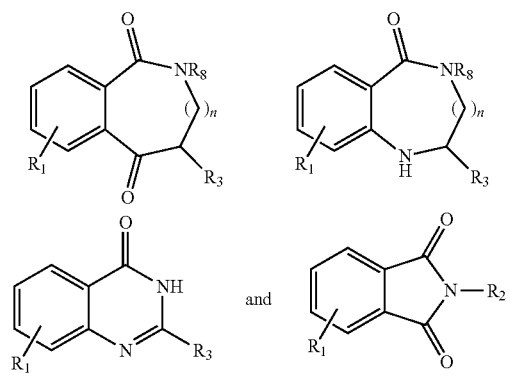

wherein $R_1$ is selected from the group consisting of H, halo, $C_1$-$C_8$ alkyl, $C_1$-$C_8$ haloalkyl, —$NR_5R_7$, hydroxy and $C_1$-$C_8$ alkoxy;

$R_2$ is selected from the group consisting of optionally substituted bicyclic, optionally substituted aryl, and

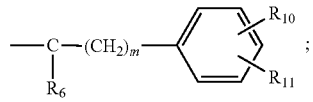

$R_3$ is selected from the group consisting of

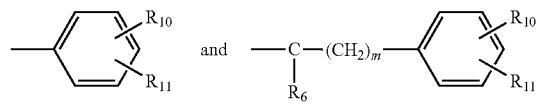

$R_8$ is selected from the group consisting of H and $C_1$-$C_8$ alkyl, or $R_3$ and $R_8$ taken together, can form with the adjacent ring, an optionally substituted 5- or 6-membered aromatic ring;

$R_{10}$ and $R_{11}$ are independently selected from the group consisting of H, halo, $C_1$-$C_8$ alkyl, $C_1$-$C_8$ haloalkyl, —$NR_5R_7$, hydroxy and $C_1$-$C_8$ alkoxy or $R_{10}$ and $R_{11}$ taken together, can form, with the adjacent ring, an optionally substituted $C_5$-$C_6$ cycloalkyl or an optionally substituted $C_5$-$C_6$ aromatic ring;

$R_5$ and $R_7$ are independently H, or $C_1$-$C_8$ alkyl;

$R_6$ is selected from the group consisting of H, or $C_1$-$C_8$ alkyl, $C_2$-$C_8$ alkenyl and $C_2$-$C_8$ alkynyl;

n is an integer ranging from 0-2; and m is an integer ranging from 0-6.

In one embodiment a method of inhibiting angiogenesis comprises administering a compound having the general structure:

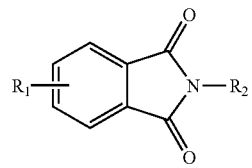

wherein $R_1$ is H, halo or $C_1$-$C_4$ haloalkyl;

$R_2$ is selected from the group consisting of

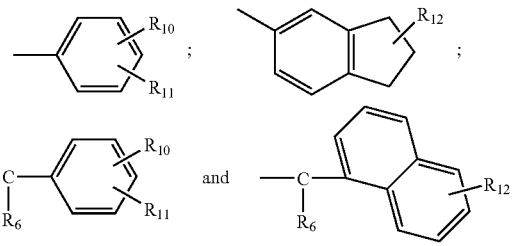

wherein $R_{10}$ and $R_{11}$ are independently selected from the group consisting of H, halo, $C_1$-$C_4$ haloalkyl, —$NR_5R_7$, hydroxy and $C_1$-$C_8$ alkoxy;

$R_5$ and $R_7$ are independently H, or $C_1$-$C_4$ alkyl;

$R_{12}$ is selected from the group consisting of H, halo and $C_1$-$C_8$ alkoxy; and $R_6$ is $C_1$-$C_8$ alkyl. In one embodiment $R_{10}$ and $R_{11}$, are independently H, halo or $C_1$-$C_4$ alkoxy, $R_1$ and $R_{12}$ are H, and $R_6$ is $C_1$-$C_6$ alkyl.

In accordance with one embodiment the thalidomide derivative compounds of the present invention can be formulated as pharmaceutical compositions by combining the compounds with one or more pharmaceutically acceptable carriers. These formulations can be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of a tumor. Biodegradable polymers suitable for use with the present invention are known to the skilled practitioner and are described in detail, for example, in Brem et al., J. Neurosurg. 74:441-446 (1991).

In addition to the use of such pharmaceutical compositions as anti-angiogenic compounds, the thalidomide derived compounds and corresponding compositions also have utility as sodium channel blockers, calcium channel blockers, contraceptives, anti-inflammatory agents and anti-cancer agents. In one embodiment a composition comprising a thalidomide derivative of the present invention is used to treat age related macular degeneration.

In accordance with one embodiment the present composition are administered either orally or parenterally. When administered orally, the compounds are administered as a liquid solution, powder, tablet, capsule or lozenge. The compounds can be used in combination with one or more conventional pharmaceutical additives or excipients used in the preparation of tablets, capsules, lozenges and other orally administrable forms. When administered parenterally, and more preferably by intravenous injection, the derivatives of the present invention can be admixed with saline solutions and/or conventional IV solutions.

The dosage of the active compound will depend on the condition being treated, the particular compound, and other clinical factors such as weight and condition of the human or animal and the route of administration of the compound. It is to be understood that the present invention has application for both human and veterinary use. For oral administration to humans, a dosage of between approximately 0.1 to 300 mg/kg/day, preferably between approximately 0.5 and 50 mg/kg/day, and most preferably between approximately 1 to 10 mg/kg/day, is generally sufficient.

It should be understood that in addition to the active anti-angiogenic compounds, the compositions of the present invention may include other agents conventional in the art including solubilizing agents, inert fillers, diluents, excipients and flavoring agents.

In accordance with one embodiment, diseases associated with corneal neovascularization can be treated by administering a composition comprising a compound having the general structure:

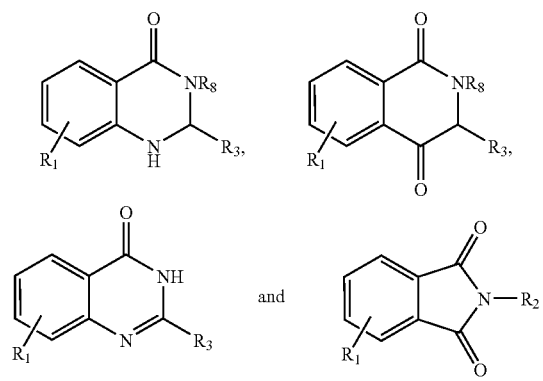

wherein $R_1$ is selected from the group consisting of H, halo, alkyl, haloalkyl, $-NR_5R_6$, hydroxy and alkoxy;

$R_2$ is selected from the group consisting of

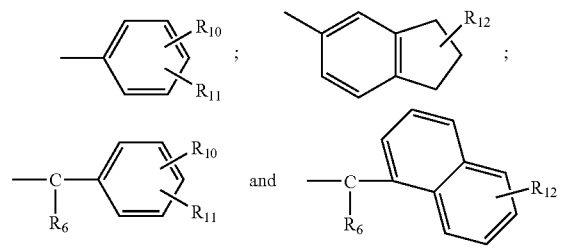

$R_3$ is selected from the group consisting of

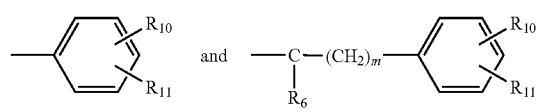

$R_8$ is selected from the group consisting of H and alkyl, or $R_3$ and $R_8$ taken together, can form with the adjacent ring, an optionally substituted $C_5$-$C_6$ cycloalkyl or $C_5$-$C_6$ aromatic ring;

$R_{10}$ and $R_{11}$ are independently selected from the group consisting of H, halo, $C_1$-$C_4$ haloalkyl, $-NR_5R_7$, hydroxy and $C_1$-$C_8$ alkoxy or $R_{10}$ and $R_{11}$ taken together, can form with the adjacent ring, an optionally substituted $C_5$-$C_6$ cycloalkyl or optionally substituted $C_5$-$C_6$ aromatic ring;

$R_5$ and $R_7$ are independently H, or $C_1$-$C_4$ alkyl;

$R_{12}$ is selected from the group consisting of H, halo and $C_1$-$C_8$ alkoxy;

m is an integer ranging from 0-4; and $R_6$ is $C_1$-$C_8$ alkyl. In one embodiment the compound has the general structure

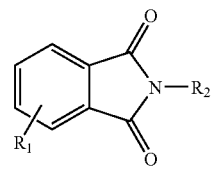

wherein $R_1$ is H or halo; and $R_2$ is selected from the group consisting of

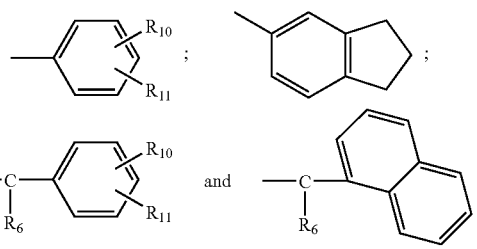

wherein $R_{10}$ and $R_{11}$ are independently H, halo or $C_1$-$C_4$ alkoxy, $R_1$ and $R_{12}$ are H, and $R_6$ is $C_1$-$C_6$ alkyl.

Another disease which can be treated according to the present invention is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

The thalidomide derived compounds of the present invention are also anticipated to have use in treating a wide variety of diseases or conditions that are related to angiogenesis, including diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scieritis, Steven's Johnson disease, pemphigold radial keratotomy, and corneal graph rejection. Diseases associated with retinal/choroidal neovascularization that can also be treated according to the present invention and include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

EXAMPLE 1

Molecular modeling was used to facilitate the design of a novel series of isoquinolines. Initially, a one carbon addition to the imide ring was considered to prepare compounds of the general structure:

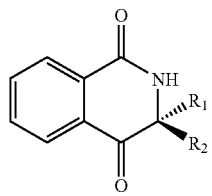

Conformational analysis of this phthalimide analog, docked in the crystal structure of polyADP-ribose polymerase, revealed the conformational similarity of the proposed structural mimic with phthalimides. With this in mind, the synthesis of two initial series of analogs was proposed as a preliminary set of synthetic targets.

| compound | $R_{20}$ | $R_{21}$ | amino acid | n |
|---|---|---|---|---|
| Series A | | | | |
| 1 | H | H | glycine | |
| 2-(±) | $CH_3$ | H | alanine | |
| 3-(±) | benzyl | H | phenylalanine | |
| 4-(±) | HO-benzyl | H | tyrosine | |
| 5 | phenyl | phenyl | | |
| 6-(±) | phenyl | H | | |
| 7-(±) | phenyl | $CH_3$ | | |
| Series B | | | | |
| 8 | | | | 2 |
| 9 | | | | 3 |
| 10 | | | | 4 |

These compounds represent first generation analogs which investigate important structure and enantioselective relationships for isoquinolines. The synthesis of mimics 1-10 is outlined in Scheme I and represents reasonable literature reported organic transformations. The utility of this synthetic scheme allows for the insertion of a large diversity of functional groups. Furthermore the synthetic design allows for the straightforward synthesis of enantiomerically pure final products through the addition of selected chiral amino acids.

Scheme I. Synethetic Scheme for Analogs in this Study

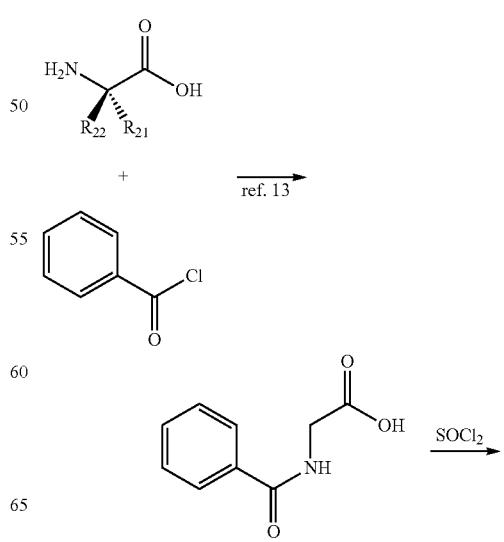

-continued

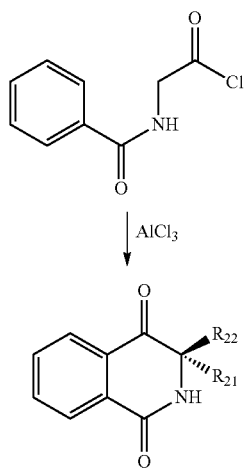

ref. 13:
J. Amer. Chem. Soc., 102(9), 340-48, 1980.

EXAMPLE 2

Additional compounds were prepared wherein the piperidine-2,6-dione moiety of thalidomide is replaced with a rigid or open ring structure having the general structure:

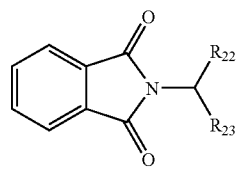

wherein $R_{22}$ is aryl and $R_{23}$ is H, $C_1$-$C_{12}$ alkyl, $C_2$-$C_{12}$ alkenyl or $C_2$-$C_{12}$ alkynyl, or $R_{22}$ and $R_{23}$ together with the intervening carbons form an aryl. The synthetic schemes used to prepare these compounds is as follows:

Synthesis of 2-Indan-5-yl-1,3-dioxo-2,3-dihydro-1H-isoindole-5-carboxylic Acid

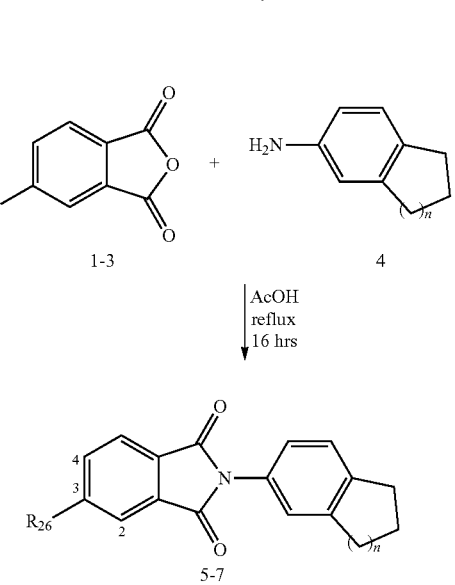

| Compd # | $R_{26}$ | n | yield |
|---------|----------|---|-------|
| 5 | H | 1 | 67% |
| 6 | 3-COOH | 1 | 60% |
| 7 | H | 2 | 49% |

Compounds 5-7 can also be prepared by the following reaction:

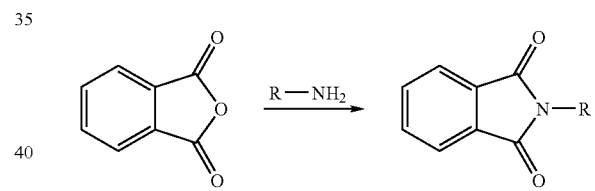

Synthesis of 2-(1,2,3,4-Tetrahydro-naphthalen-1-yl)-isoindole-1,3-dione

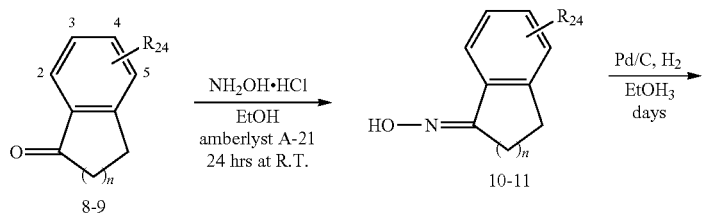

| Compound # | $R_{24}$ | n | Compd # | $R_{24}$ | n | yield |
|------------|----------|---|---------|----------|---|-------|
| 8 | H | 3 | 10 | H | 3 | 78% |
| 9 | 3-F | 3 | 11 | 3-F | 3 | 100% |

-continued
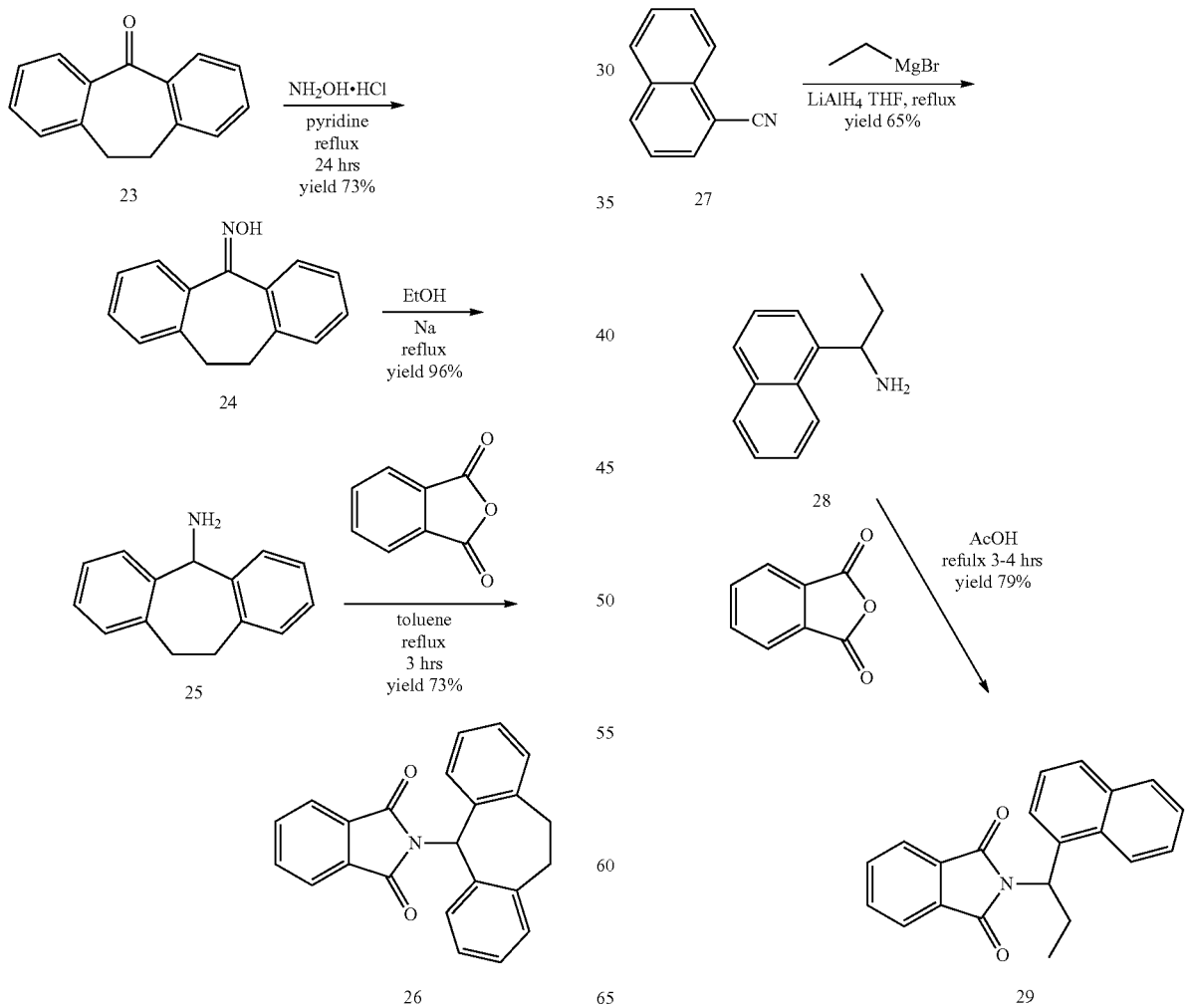
| Compd # | R24 | n | yield | Compd # | R24 | R25 | n | yield |
|---|---|---|---|---|---|---|---|---|
| 12 | H | 1 | | 16 | | | 1 | 98% |
| 13 | H | 3 | 70% | 17 | H | H | 3 | 100% |
| 14 | H | 3 | | 18 | H | 3-CH3 | 3 | 76% |
| 15 | 3-F | 3 | 48% | 19 | 3-F | 2-F | 3 | 62% |
| | | | | 20 | 3-F | 3-CH3 | 3 | 50% |
| | | | | 21 | H | 2-F | 3 | 72% |
| | | | | 22 | H | H | 2 | 84% |
Synthesis of 2-(10,11-Dihydro-5H-dibenzo[a,d]cyclohepten-5-yl)-isoindole-1,3-dione
Synthesis of 2-(1-Naphthalen-2-yl-propyl)-isoindole-1,3-dione

21
Synthesis of 2-[1-(3,4-Dimethoxy-phenyl)-heptyl]-isoindole-1,3-dione
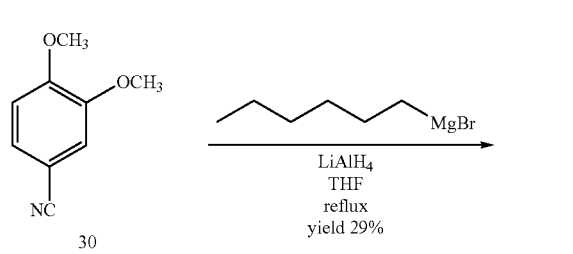
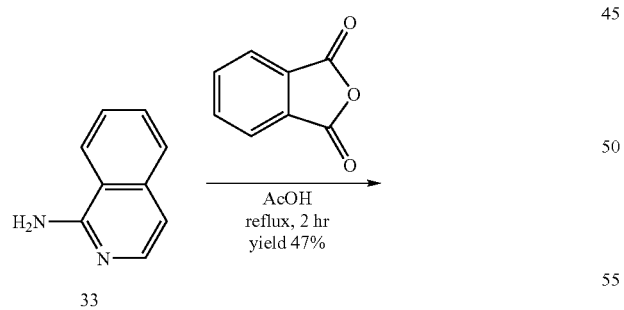
Synthesis of 2-Isoquinolin-1-yl-isoindole-1,3-dione
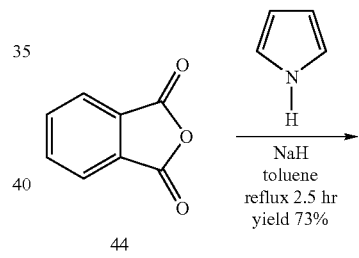
22
Synthesis of N-(2-phenylethyl)-phthalimide
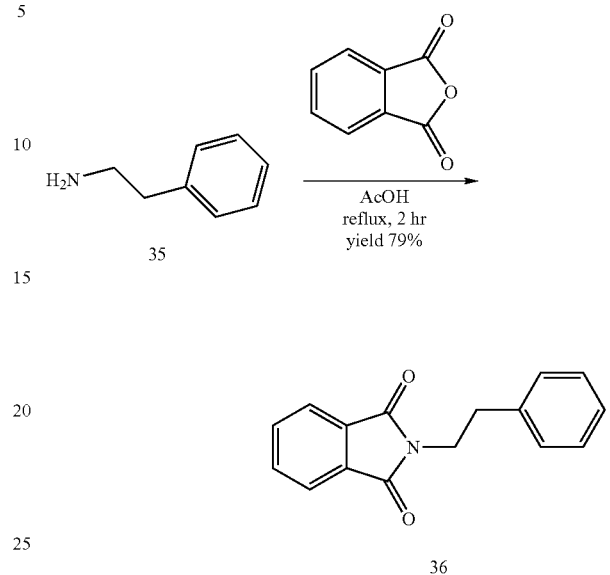
Synthesis of Phenyl Substituted-Phthalimides
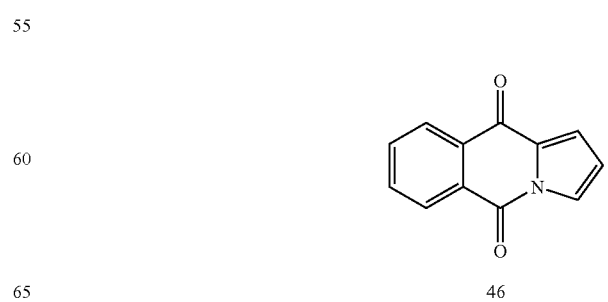

23
Synthesis of 4-Hydroxy-2H-isoquinolin-1-one
24
Synthesis of Pyrrolo[1,2-b]isoquinoline-5,10-dione
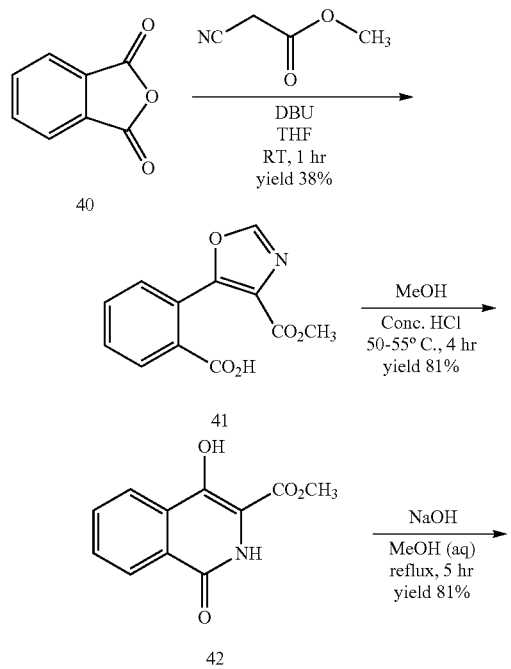
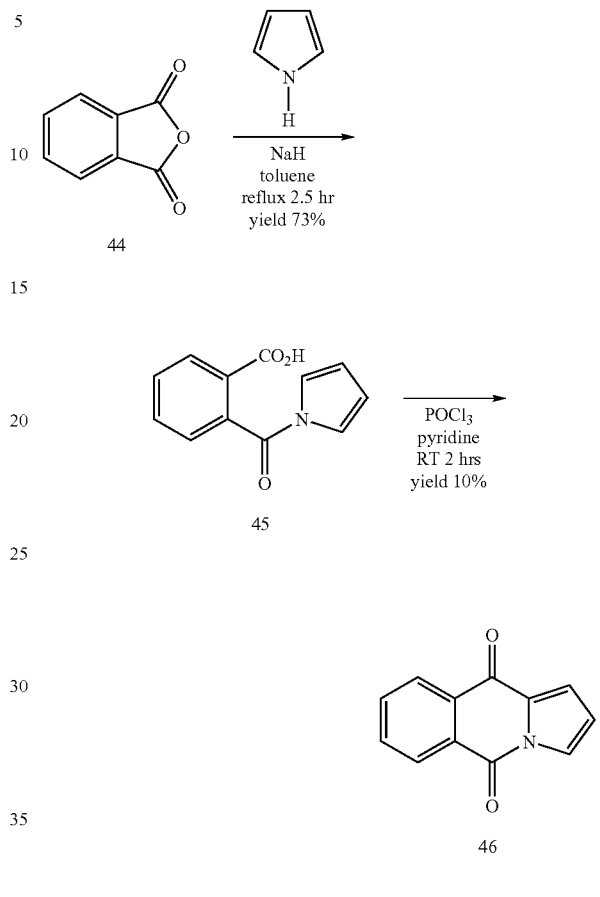
Synthesis of 3H-quinazolin-4-ones
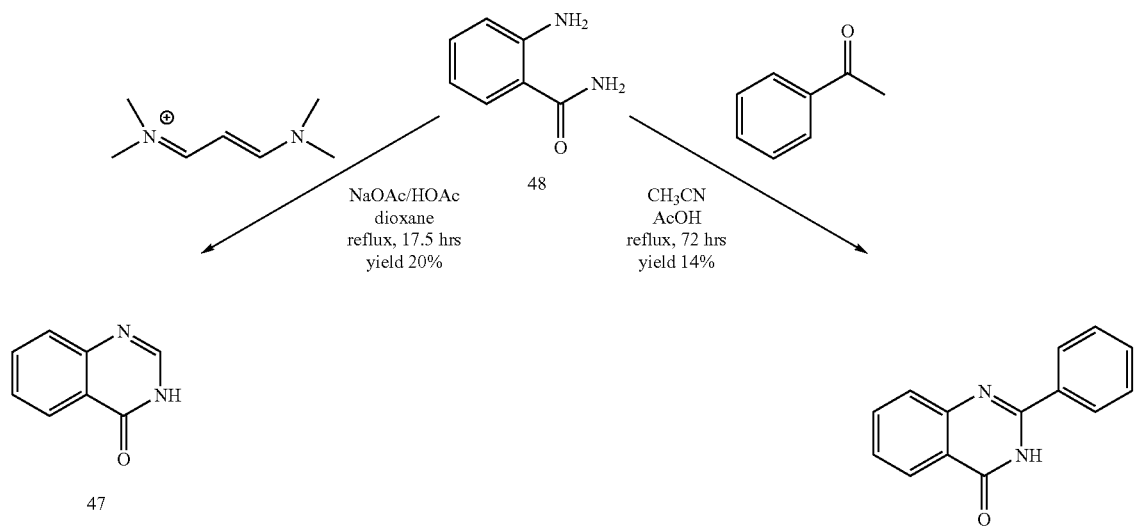

These compounds will be evaluated for their ability to inhibit corneal neovascularization and endothelial cell proliferation.

EXAMPLE 3

Endothelial Cell Proliferation Assay.

The human vascular endothelial cells (HUVECS) were cultured to peri-confluence (80%) in 20% serum and treated with thalidomide (standard) or its analog (40-400 µM). After 20 h, [$^3$H]-thymidine (2 µCi/ml) was added to the culture medium for 2-4 h. The [$^3$H]-thymidine incorporation was stopped with ice-cold PBS (3 washes) and the cells were incubated with cold 10% trichloroacetic acid (TCA) for 10 min at 4° C. The cells were further incubated with TCA at room temperature for 10 min and washed three times with PBS. The cells were solubilized overnight with 1N NaOH and neutralized with an equivalent amount of 1N HCl before radioactivity was determined. The anti-proliferative activity of thalidomide or its analog was computed as a percent inhibition of HUVECS mitogenic response to 20% serum (fetal calf serum).

Evaluation of thalidomide for inhibition of the incorporation of $^3$H-thymidine into endothelial cells reveal this compound to have an $IC_{50}$ of 200 µM. Preliminary $IC_{50}$ data for the first panel of compounds reveal four compounds (5, 29, 32 and 50) to have 2-4 times greater potency than thalidomide in inhibiting 3H-thymidine incorporation into endothelial cells (See Table 1). This structure activity relationship (SAR) establishes that the piperidine-2,6-dione moiety is not needed for increased inhibition of endothelial cell proliferation.

TABLE 1

Biological Data for Analogs in this Study

| Compd # | Structure | Inhibition of Endothelial Cell Proliferation ($IC_{50}$ µM) |
|---|---|---|
| 1 | Thalidomide | 200 |
| 5 | | 85 |
| 7 | | >400 |
| 49 | 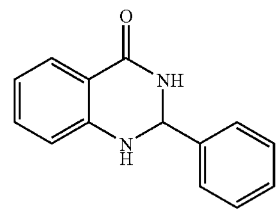 | 385 |
| 29 | 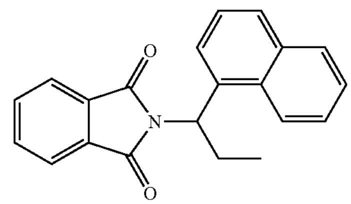 | 45 |
| 32 | 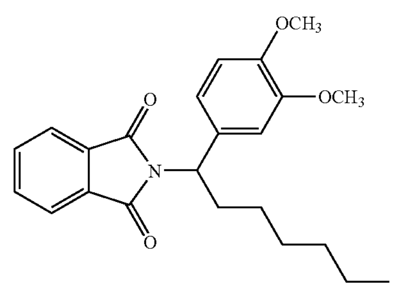 | <38.5 |
| 50* | 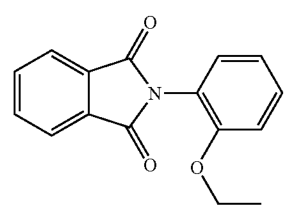 | 110 |
| 51* | 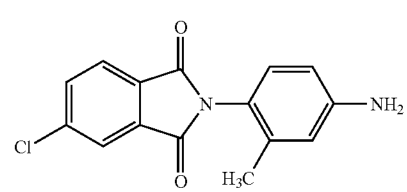 | 350 |
| 52* | 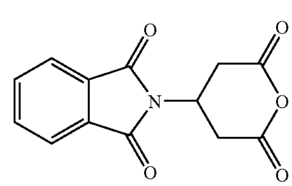 | >400 |

TABLE 1-continued

Biological Data for Analogs in this Study

| Compd # | Structure | Inhibition of Endothelial Cell Proliferation (IC$_{50}$ µM) |
|---|---|---|
| 53* | 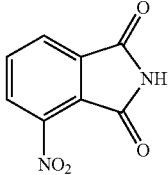 | >400 |

*Obtained from the Aldrich Chemical Library.

EXAMPLE 4

4-oxo-quinazoline derivatives having the general structure:

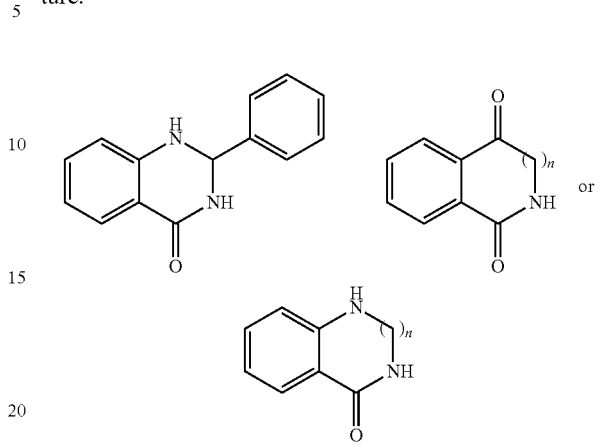

wherein n is 1-4 can be prepared according to the following schemes:

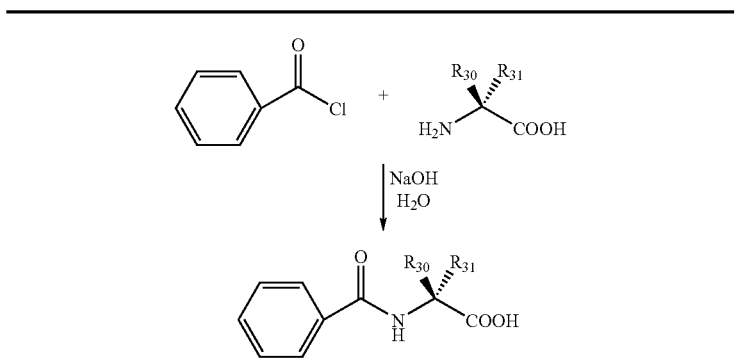

| Compound | chiral center | R$_{30}$ | R$_{31}$ | % yield |
|---|---|---|---|---|
| 33 | | H | H | 76 |
| 34 | R | C$_6$H$_5$ | H | 83 |
| 35 | S | C$_6$H$_5$ | H | 75 |
| 36 | S | HOC$_6$H$_4$ | H | — |
| 37 | R | CH$_3$ | H | 42 |
| 38 | S | CH$_3$ | H | 68 |
| 39 | S | CH$_2$C$_6$H$_4$ | H | 90 |
| 40 | R | CH$_2$C$_6$H$_4$ | H | 16 |

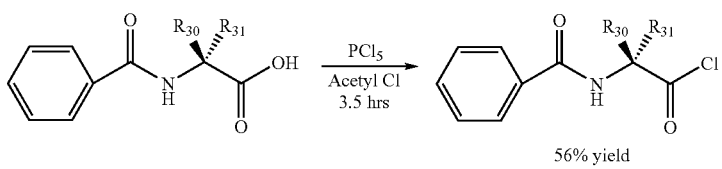

56% yield

-continued

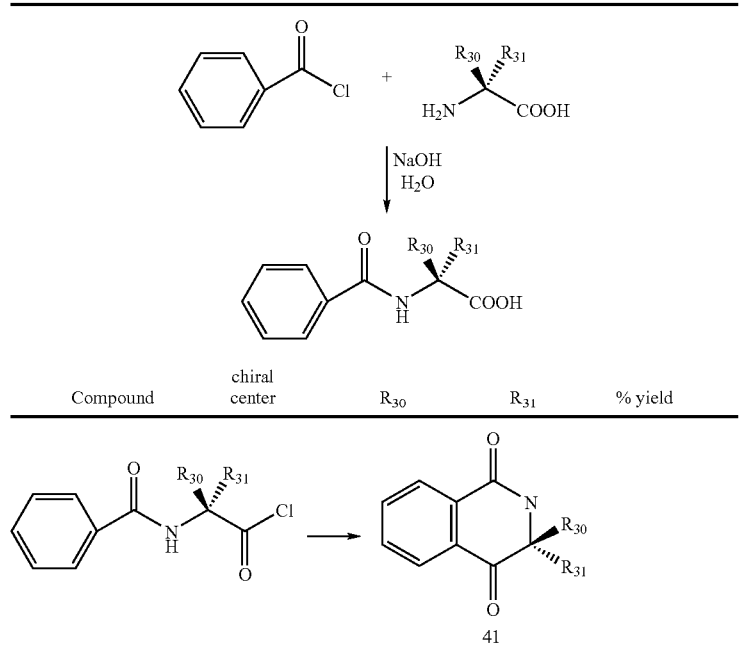

| Compound | chiral center | $R_{30}$ | $R_{31}$ | % yield |
|---|---|---|---|---|

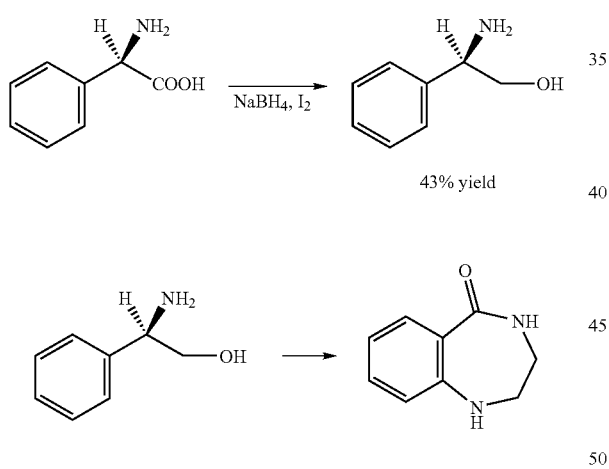

Preparation of expanded ring structures:

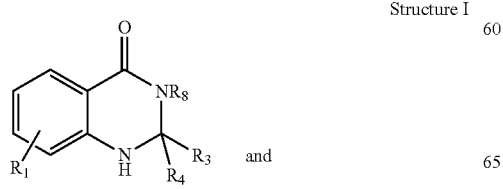

43% yield

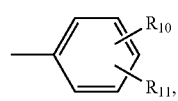

The invention claimed is:

1. A compound represented by a general structure selected from the group consisting of structure I and structure II:

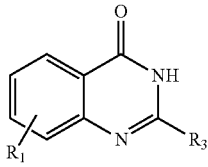 and

Structure I

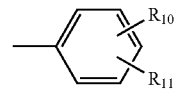

Structure II wherein $R_1$ is selected from the group consisting of H, $C_1$-$C_4$ alkyl, and $C_1$-$C_8$ alkoxy;

$R_3$ is $R_8$ is H;

$R_4$ is selected from the group consisting of H, $C_1$-$C_8$ alkyl, phenyl and benzyl;

$R_{10}$ and $R_{11}$ are independently selected from the group consisting of H, bromo, ortho-Cl, meta-Cl, fluoro, iodo, $C_2$-$C_8$ alkyl, $C_1$-$C_8$ haloalkyl, hydroxy and $C_2$-$C_8$ alkoxy or $R_{10}$ and $R_{11}$ taken together, can form with the adjacent ring, $C_5$-$C_6$ cycloalkyl or $C_5$-$C_6$ aromatic ring, wherein when either of $R_{10}$ or $R_{11}$ are hydrogen, the other is not hydrogen, alkyl, or amino; provided that when $R_3$ is neither $R_{10}$ or $R_{11}$ is a trifluoromethyl, hydroxy, bromo, chloro, fluoro, iodo, $NH_2$, or $C_2$-$C_8$ alkyl group, or $C_2$-$C_3$ alkoxy group ortho to the point of attachment of $R_3$ to structure I or structure II, nor are $R_{10}$ and $R_{11}$ both hydrogen;

$R_5$ and $R_7$ are independently H, or $C_1$-$C_8$ alkyl;

$R_6$ is selected from the group consisting of H, or $C_1$-$C_{12}$ alkyl, $C_2$-$C_8$ alkenyl and $C_2$-$C_8$ alkynyl;

2. The compound of claim 1 wherein
$R_1$ is H;
$R_3$ is selected from the group consisting of

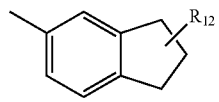

$R_4$ and $R_8$ are H;
$R_6$ is $C_1$-$C_8$ alkyl;
$R_{10}$ and $R_{11}$ are independently selected from the group consisting of H, and $C_2$-$C_8$ alkoxy or $R_{10}$ and $R_{11}$ taken together, can form with the adjacent ring, $C_5$-$C_6$ cycloalkyl or $C_5$-$C_6$ aromatic ring;
m is 1 or 0.

3. A pharmaceutical composition comprising the compound of claim 1 and a pharmaceutically acceptable carrier.

4. A pharmaceutical composition comprising a compound represented by the general structure:

Structure I

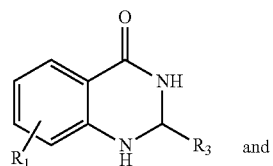

and

Structure II

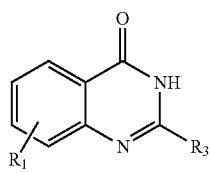

wherein $R_1$ is H;
$R_3$ is

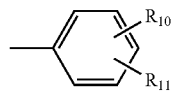

$R_{10}$ and $R_{11}$ are independently selected from the group consisting of H, bromo, ortho-Cl, meta-Cl, fluoro, iodo, $C_2$-$C_8$ alkyl, $C_1$-$C_8$ haloalkyl, hydroxy and $C_2$-$C_8$ alkoxy or $R_{10}$ and $R_{11}$ taken together, can form with the adjacent ring, $C_5$-$C_6$ cycloalkyl or $C_5$-$C_6$ aromatic ring, wherein when either $R_{10}$ or $R_{11}$ are hydrogen, the other is not hydrogen, alkyl, or amino;

provided that
when $R_3$ is

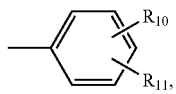

neither $R_{10}$ or $R_{11}$ is a trifluoromethyl, hydroxy, bromo, chloro, fluoro, iodo, or $C_2$-$C_8$ alkyl group, or $C_2$-$C_3$ alkoxy group ortho to the point of attachment of $R_3$ to structure I or structure II, nor are $R_{10}$ and $R_{11}$ both hydrogen;

$R_5$ and $R_7$ are independently H, or $C_1$-$C_8$ alkyl;

$R_6$ is selected from the group consisting of H, or $C_1$-$C_{12}$ alkyl, $C_2$-$C_8$ alkenyl and $C_2$-$C_8$ alkynyl;

and a pharmaceutically acceptable carrier.

* * * * *